United States Patent [19]

Lambiez et al.

[11] Patent Number: 5,605,703
[45] Date of Patent: Feb. 25, 1997

[54] LIPOSOMES ENCAPSULATING DOXORUBICIN

[75] Inventors: Fernando P. Lambiez, Nocius de Rei; Raquel D. Gonzalez, Barcelona; Antonio P. Dueña, Saint Just Desvern, all of Spain

[73] Assignee: Lipotec, S.A., Spain

[21] Appl. No.: 346,236

[22] Filed: Nov. 23, 1994

[30] Foreign Application Priority Data

Nov. 25, 1993 [ES] Spain .................................. 9302481

[51] Int. Cl.$^6$ ................................................ A61K 9/127
[52] U.S. Cl. ........................................................ 424/450
[58] Field of Search ........................................... 424/450

[56] References Cited

U.S. PATENT DOCUMENTS 5,318,987  6/1994  Weithman ........................ 514/457

FOREIGN PATENT DOCUMENTS 0274174  7/1988  European Pat. Off. .
WO85/00968  3/1985  WIPO .
WO92/02208  2/1992  WIPO .

OTHER PUBLICATIONS

"Inhibition of Rat Liver Microsomal Lipid Peroxidation Elicited by 2,2–Dimethylchromenes and Chromans Containing Fluorinated Moieties Resistant to Cytochrome P–450 Metabolism", *Biorganic & Medicinal Chemistry*, vol. 1, No. 3, pp. 219–225, Oct. 2, 1993.

"Inhibition of Rat Liver Microsomal Lipid Peroxidation Elicited by Simple 2,2–Dimethylchromenes and Chromans Structurally Related to Precocenes", *J. Agric. Food Chem.*, 1992, 40, 585–590.

International Search Report, Nov. 1996.

*Primary Examiner*—Gollamudi S. Kishore
*Attorney, Agent, or Firm*—Wigman, Cohen, Leitner & Myers, PC

[57] ABSTRACT

Liposomes encapsulating doxorubicin, which contain, incorporated into them, a protector compound of general formula A or B, in order to reduce the toxicity of the drug when it is administered in intravenous form, and in which formulas $R_1$ and $R_2$, are the same or different, independently represented by HO—, $CH_3O$— or $CF_3CH_2O$—

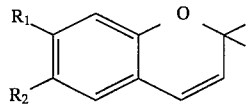

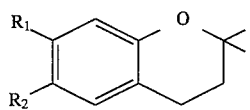

23 Claims, 4 Drawing Sheets

FIG. 6

LIPOSOMES ENCAPSULATING DOXORUBICIN

SUMMARY OF THE INVENTION

This invention is related to anti-neoplastic agents and in particular to the encapsulation of the same in liposomes which contain anti-free radical agents to reduce the toxicity of the drug.

BACKGROUND OF THE INVENTION

The antibiotic doxorubicin (DXR) and its derivatives, as well as other cationic anthracyclines currently are of great clinical interest in the treatment of cancer, including leukemias and solid tumors.

Furthermore great hopes have centered around the use of liposomes as transport systems for bioactive agents. In these systems the drug is incorporated into the aqueous portion of the liposomes when it is hydrophilic or is distributed between the aqueous portion and the lipidic bilayers of the liposome when the drug shows a greater lipophilic nature. Once the drug is encapsulated, it can be administered to the patient to be treated.

It has been established by various investigators that the use of liposomes for the administration of antineoplastics in many cases improves the traditional methods of administration, see for example: Gabizon et al.: Cancer Res. (1982) 42, 4734–4739 and Van Hossel et al.: Cancer Res. (1984) 44, 3698–3705 (both herein incorporated by reference).

It has been observed by means of the utilization of various animal models that the encapsulation of doxorubicin in liposomes significantly reduces the secondary effects of toxicity, both chronic and acute. See, by way of example, Rahman et al.: Cancer Res. (1980) 40, 1532–1537, Forssen et al.: Proc. Natl. Acad. Sci. USA (1981) 78, 1873–1877, Olson et al.: Eur. J. Cancer Clin. Oncol. (1982) 18, 167–176, Rahman et al.: "Cancer" Res. (1985) 45, 796–803 and Gabizon et al.: J. Natl. Cancer Inst. (1986) 77, 459–467 (all herein incorporated by reference). Additionally, other indicators of toxicity, such as alopecia, loss of weight, nausea, vomiting, and also the dermal necrosis produced by extravasation may be reduced in significant manner by the administration of doxorubicin in liposomes. Forssen et al.: Cancer Treat. Rep. (1983) 67, 481–484,(herein incorporated by reference) see also the references cited previously in this paragraph.

Also, it has been established in various tumor models that this significant reduction of the toxicity is not produced at the expense of a reduction of the anti-tumor efficacy. Besides the references previously noted, see Rahman et al.: Chemoter, Pharmacol. (1986) 16, 22–27, Gabizon et al.: Cancer Res. (1983) 43, 4730–4735 and Br. J. Cancer (1985) 51, 681–689, Maythew et al.: J. Natl. Cancer Inst. (1987) 78, 707–713, Forssen et al.: Cancer Res. (1983) 43,546–550, and Storm et al.: Cancer Res. (1987) 47, 3366–3362 (all herein incorporated by reference).

The cardiomyopathy observed in treatments with doxorubicin is similar to the lesions seen in the cardiac muscles in experimental animals under conditions of alpha-tocopherol deficiency, Tomasz: Chem-Biol Interact. (1976) 13, 89. These results suggest that the lesions produced by the drug are caused by an increase in free-radical reactions in which lipids of membrane are seen to be involved. Therefore, the incorporation of doxorubicin, herein after DXR, into the lipidic bilayers of the liposomes may facilitate the unleashing of free-radical type reactions.

It has been observed that the incorporation of alpha-tocopherol in liposomes which contain DXR reduces the toxicity in animals and produces less cardiomyopathy than when combinations of alpha-tocopherol/DXR or liposomes/DXR in separate form are administered. Olson et al.: Eur. J. Clin. Oncol. (1982) 12(2). 167 (herein incorporated by reference). The reduction of toxicity achieved by means of the co-encapsulation of alpha-tocopherol and DXR in liposomes seems to result from a combination of the alteration in the biodistribution of the drug, due to the encapsulation of it in liposomes, and to a reduction of the damaging effect of the free radicals, due to the capture of these by the alpha-tocopherol.

Different patents describe the inclusion of anti-free radical agents into liposomes:

| WO 85/00968, | WO 85/04578, | WO 87/02219 |
| WO 87/04592 | WO 88/09168 and | EP 274 174 |

(all herein incorporated by reference).

In most of the patents cited in general the presence of alpha-tocopherol is claimed, its salts and/or esters, even though other compounds like N-acetylcysteine, niacin, isocitrate or BHT have also been claimed.

Therefore, the search for compounds with improved activity as inhibitors of the lipid peroxidation is an active field of investigation. In this sense, a family of analogs of the Vitamin E with an excellent activity of elimination of free radicals has been described by Battoni et al.: Biochem. Biophys. Res. Commun. (1991) 174, 1103. In the same context in this patent the inhibiting activity of the lipidic peroxidation of compounds with structure of 2,2 dimethylchromenes and chromans is described, which are potentially applicable for stabilization of preparations in which anthracyclines in liposomes are incorporated, resulting in a notable reduction of the undesired effects of the drug.

SUMMARY OF THE INVENTION

Figure 1:
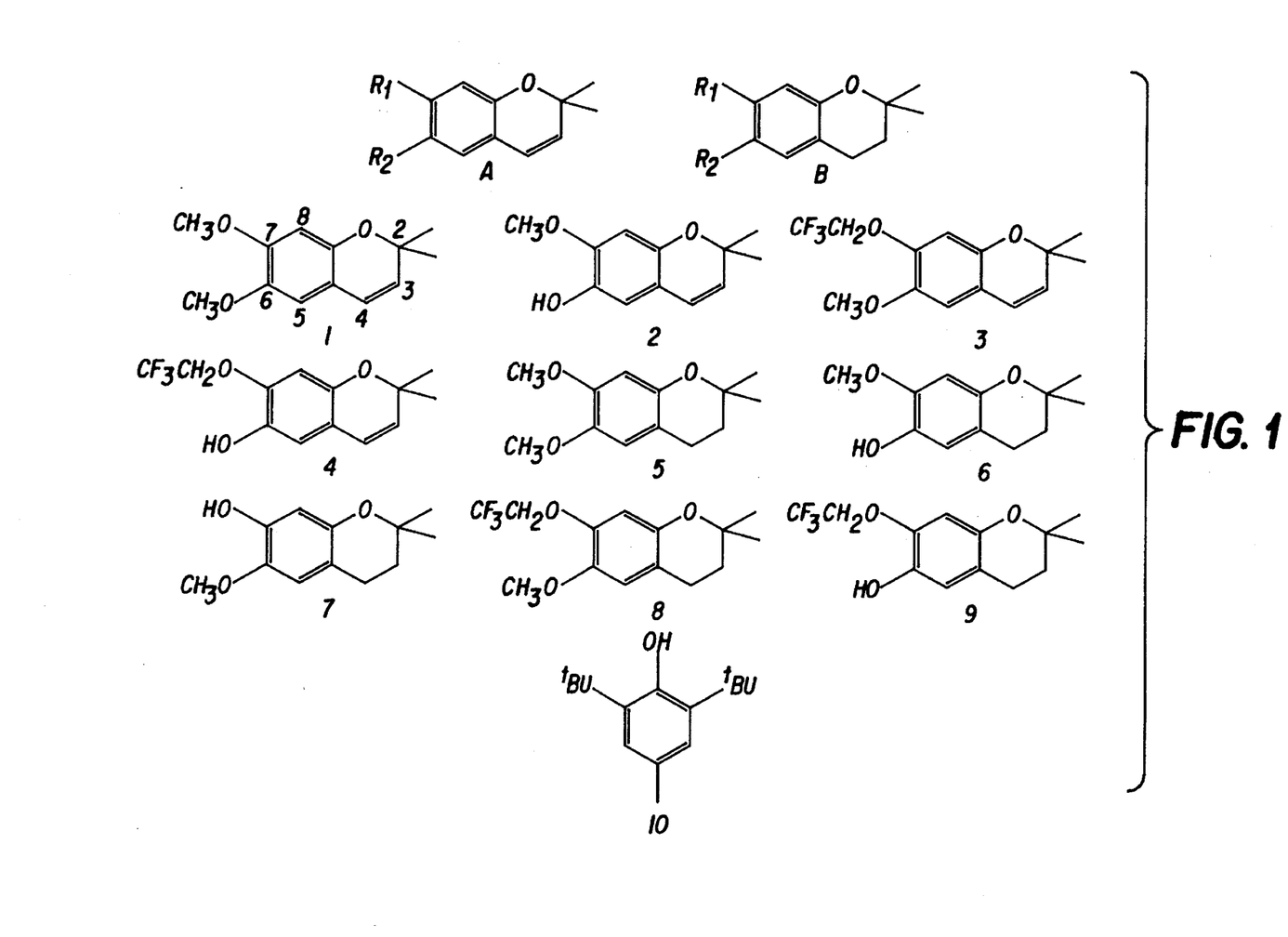
FIG. 1 illustrates the formulas of the chromenes (1–4), chromans (5–9) and compound of reference, BHT, (10) studied as inhibitors of the lipidic peroxidation.

In view of the foregoing state of the art, it is a general objective of this invention to obtain a formulation for anthracyclines in liposomes, containing therein inhibitors of the lipidic peroxidation of general formula A or B (FIG. 1).

One objective of the invention is to provide a composition of anthracyclines in liposomes which substantially reduce the effects of peroxidation both of the lipids and of the drug.

A principal objective of this patent is to obtain a composition of doxorubicin, its salts and analogous compounds in liposomes, in order to reduce the toxicity of the drug, which is related to reactions of oxidation and free radicals.

A final objective of the invention is to provide a method for treating human neoplasms, and particularly, primary or metastatic tumors in the liver, proliferative hematopoietic disorders and leukemias with DXR encapsulated in liposomes with a significant reduction of the normal secondary effects of the drug.

The invention includes the formation of liposomes characterized by:

a) A lipidic concentration between 10 and 100 mg/ml, and preferably around 50 mg/ml.

b) The components lipids are phospholipids, both of natural and synthetic origin; and cholesterol.

c) The proportion of cholesterol, with respect to the total quantity of lipids, is between 0 and 50%, preferably between 35 and 50%.

d) The phospholipids present are phosphatidylcholine, which does not show net charge and another phospholipid charged negatively, for preference the phosphatidylglycerol.

e) The relationship of the neutral phospholipid to the negatively charged one falls between 10:2 and 10:10 and for preference between 10:7 and 10:10, respectively.

f) The relationship of the protective agent of general formula A or B (FIG. 1) to lipids falls between 0.01 and 15%.

g) The liposomes are formed in an aqueous solution, buffered or not, physiologically isotonic. For example NaCl 0.9%.

The characteristics of the liposomal suspension encapsulating doxorubicin, thus obtained, are those listed below:

a) They incorporate the characteristics cited.

b) The percentage of encapsulated drug is between 70 and 90% of the initial quantity.

c) It is stable, reproducible and possible to industrialize with respect to its size and the quantity of doxorubicin encapsulated.

d) The liposomal suspension, under these conditions, is usable in cancer therapy.

In the specification and drawings, the abbreviations have the following meanings:

| | |
|---|---|
| DXR | Doxorubicin |
| PC | Phosphatidylcholine |
| PL | Hydrogenated Phospholipids of egg |
| DPPC | Dipalmitoylphosphatidylcholine |
| PG | Phosphatidylglicerol |
| DPPG | Dipalmitoylphosphatidylglycerol |
| CHOL | Cholesterol |
| F-DXR | Free DXR |
| L-DXR | DXR encapsulated in liposomes |
| L(C6)-DXR | DXR encapsulated in liposomes which contain chroman 6 |
| L(C6) | Liposomes which contain chroman 6 (they do not contain DXR) |

DETAILED DESCRIPTION OF THE INVENTION

Preparation of liposomes containing doxorubicin (DXR).

a) Lipidic components

The lipids which form liposomes are widely known. Generally phospholipids are included, with a net neutral and/or negative charge, and a sterol, such as cholesterol. The election of the lipids is made on the basis of the needs with respect to the final liposomal size, the drug to be encapsulated and the stability which is desired for the preparation. Usually, the greatest lipidic component of the liposomes is phosphatidylcholine (PC). The PCs differ among themselves in the length and degree of saturation of their acyclic chains and they can be isolated from natural or synthesized sources. The inclusion of a negatively charged phospholipid favors the stability of the liposomal solution, preventing the spontaneous aggregation of the liposomes. The phospholipids with negative charge most utilized are the phosphatidylglycerol (PG), phosphatidylserine (PS) and phosphatidylinositol (PI), among others. The proportion utilized of neutral phospholipid to phospholipid with negative charge goes from 10:2 to 10:10 respectively. Inclusion of cholesterol generally favors the stability of liposomes decreasing the permeability of the membrane to ions and small polar molecules, and likewise reduces the capacity of penetration of a series of proteins among the bilayers which could determine a greater disorder therein. Typically the proportion of cholesterol utilized goes from 0 to 50% of the total lipids.

b) Inhibitors of the lipidic peroxidation.

The compounds described in this invention as inhibitors of the reactions of lipidic peroxidation are a series of 2,2-dimethylchromenes and chromans of general formulas A and B (FIG. 1), respectively, and which preferentially respond to the chemical formulas (1–9) presented in FIG. 1. From among these, the fluorate compounds and especially the compounds 3, 4, 8 and 9 have not been described previously in the literature.

In view of the results obtained in EXAMPLE 1 of this invention, the potent inhibiting effect of the lipidic peroxidation which the cited compounds show remains sufficiently demonstrated. Additionally, an appropriate combination between the protection against the oxidative metabolism by means of the introduction of substitute fluorates in selected positions and the existence of a free hydroxyl group in C6 (already present or potentially generated by means of metabolic desalquilation) conduces to inhibitors of the lipidic peroxidation, compounds 6 and 9, presenting more persistent intrinsic activity, or to an anti-oxidant efficiency more metabolic-dependent compounds 5 and 8.

Figure 6:
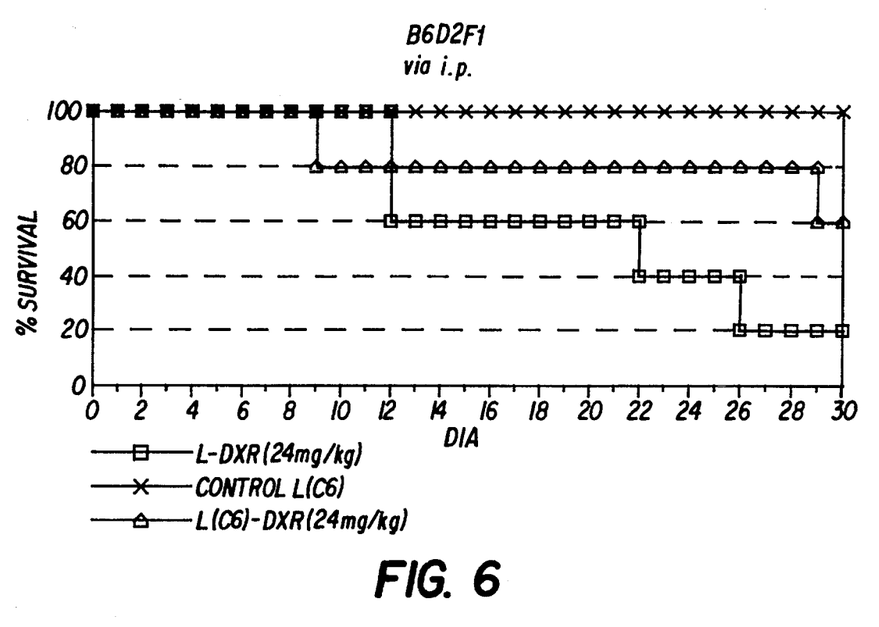
FIG. 6 represents survival curves in healthy B6D2F1 rats for the i.p. administration of L(C6), L(C6)-DXR and L-DXR.

Utilization of this type of compounds in liposomes in order to reduce the toxicity of the DXR remains clearly demonstrated in EXAMPLES 4 and 5. The inclusion of chroman 6 in liposomes which contain DXR determines a significant reduction of the toxicity of the DXR encapsulated with respect to liposomes which do not contain chroman 6, FIG. 6.

c) Preparation of the liposomes.

A preferred method is the one which Bangham et al. presented: J. Mol. Biol. (1964) 8, 660–668, herein incorporated by reference, in which multilamenar liposomes (MLVs) are obtained of heterogeneous size. In this method the formative lipids are dissolved in a suitable organic solvent which later is eliminated by rotary evaporation under vacuum. The lipid film formed is subjected to hydratation with a suitable aqueous medium containing the drug, by means of manual or mechanical agitation. The heterogeneous suspension of MLVs is subject to any of the known techniques of reduction and homogenization of sizes. For example, two preferred procedures are the sonication with titanium probes or extrusion through filters of polycarbonate of the solution of MLVs in order to obtain VETs liposomes.

By way of illustration but not limiting the scope of the invention, practical examples are described below.

EXAMPLE 1 a) Evaluation of the lipid peroxidation in rat liver microsomes.

Incubations. Suspension of Sprague-Dawley male rat liver microsomes in Krebs-Ringer (KRP) phosphates buffer, were prepared in accordance with the method of Fraga et al.: Free Radical Biol. Med. (1988) 4, 155–161. For the experiences of lipidic peroxidation induced enzymatically, microsomal protein (2 mg) in 1 ml of KRP buffer was incubated for one hour at 37° C. in the presence of 0.1 mM NADPH and 2 μl of DMSO containing the compound to be evaluated at the appropriate concentration. In the experiments where the incubations were prolonged up to three hours, every hour 0.1 ml of NADPH 2 mM was added to the incubation medium. For the experiments of lipid peroxidation induced chemically, 2 mg. of microsomal protein in 1 ml of KRP buffer were incubated for 30 min. at 37° C. in the presence of $FeSO_4$ 50/μM, ascorbic acid 0.5 mM and 2 μl of DMSO containing the compound to be evaluated at the appropriate concentration. In all cases, the incubations were arrested by addition of 0.2 ml of BHT at 4%.

TBARS test. When the incubations were completed, the lipid peroxidation was evaluated by means of the production of substances which react with thiobarbituric acid (TBARS) as Fraga et al described.: Free Radical Biol. Meal. (1988) 4, 155–161 (herein incorporated by reference). Briefly, 0.5 ml of dodecyl sodium sulphate at 3% was added to proportions of 0.5 ml of the microsomal incubations. After mixing them, 2 ml of HCl 0.1 N, 0.3 ml of phosphotungstic acid and 1 ml of 2-thiobarbituric acid were added. The mixture was kept 30 min. at 100° C., and the TBARS were extracted with 3 ml of 1-butanol. After centrifugation, the fluorescence of the butanol phase was determined exciting at 515 nm and reading at 555 nm. The values obtained were expressed as nanomoles of TBARS (malondialdehyde equivalents). The standards of malondialdehyde were prepared from 1,1,3,3-tetramethoxypropane. The experiments were performed in triplicate. The values of $IC_5$ were determined by representation of the percentage of inhibition vs. log [I], using at least five different concentrations. The values of the percentages of inhibition were referred to the determination carried out in presence of DMSO (2 μl).

In Table I the results of the inhibition of the lipidic peroxidation shown by several 2.2-dimethylchromans and chromans, fluorated or not, in incubations of rat liver microsomes induced by NADPH or stimulated by Fe-ascorbate, are shown, expressed as values of $IC_5$ for the inhibition of the production of TBARS.

The values for BHT, compound 10, were also determined for comparative effects.

TABLE I

| | $IC_{50}$ TBARS production (μM) | |
|---|---|---|
| compound | NADPH | Fe-ascorbate |
| 1 | 11.4 | (35%)[a] |
| 2 | 1.4 | 3.8 |
| 3 | 55.4 | ND[b] |
| 4 | 3.7 | 6.0 |
| 5 | 15.0 | (17%)[a] |
| 6 | 0.3 | 1.9 |
| 7 | 3.4 | 19.0 |
| 8 | 6.0 | (5%)[a] |
| 9 | 3.9 | 5.3 |
| 10 | 0.8 | 2.7 |

[a]Values in parenthesis represent the percentages of inhibition calculated at a 0.5 mM concentration.
[b]Not determined.

The hypothesis that the inhibition of the lipidic peroxidation in rat liver microsomes in the incubations with NADPH caused by a family of 2,2 dimethylchromenes and chromans is due to a mechanism of elimination of free radicals analogous to the one which operates in the mode of action of Vitamin E is based on the results which are shown in this invention. Thus, with respect to the non-fluorate derivatives only those with a free hydroxyl group (i.e. 2, 6 and 7) showed a potent inhibiting effect when the lipidic peroxidation was induced by Fe-ascorbate (Table 1). These effects where six times smaller than those obtained in the tests depending on NADPH. A similar relation was obtained with BHT (10), compound tested by way of comparison, indicating that the discrepancies observed were due to intrinsic differences between the two methods. Furthermore, the absence of desalquilating metabolism in the incubations with Fe-ascorbate prevented the formation of phenolic species, in consequence, the 6.7-alcoxy derivatives (compounds 1 and 5) were inactive under said conditions.

As happened with the incubations with NADPH, the hydroxychroman 6 was the one which showed the greatest inhibiting power in the tests with Fe-ascorbate ($IC_{50}$=1.9 μM) and its activity was also superior to that of the BHT ($IC_{50}$=2.7 μM). Additionally, the fact that the inhibition caused by the compound 6 was of an order of magnitude greater than that of the compound 7 (which happened in the tests with NADPH), indicated the importance of a free hydroxyl group in the C6 position for a strong anti-oxidizing effect. These results are in conformity with the hypothesis of a mechanism of an action similar to that of Vitamin E.

With respect to the fluorated chromenes, the hydroxy derivative 4 exhibited the greatest inhibiting activity in the incubations with NADPH (Table 1). Therefore, its detection as a metabolite in the incubations with NADPH might justify the inhibiting activity shown by the 6.7-dialcoxy-chromene 3. With respect to the incubations with Fe-ascorbate, the compound 4 showed an inhibiting activity similar to that of the non-fluorated compound 2.

With regard to the fluorated chromans, it was observed that the inhibiting activity shown by the chroman 8 ($IC_5$=6.0 μM) was nine times greater than that corresponding to chromene 3 ($IC_{50}$=55.4 μM). Additionally, the comparison of the inhibiting activities of the compound 8 and of its non-fluorated analogous compound 5 indicates that the presence of the substitute fluorate in the C7 position improves the inhibiting effect of the lipidic peroxidation. What is more, it is worth briefly describing that the chroman 8 does not present inhibiting activity per se (See incubations with Fe-ascorbate, Table 1). Studies conducted demonstrated the presence of the chroman 9 as a metabolite of the former one. Since the hydroxy derivative 9 showed, in the incubations with NADPH, the highest inhibiting activity of the chroman fluorates tested ($IC_{50}$=3.9 μM), the idea of this as responsible for the potent inhibiting activity shown by the 6,7 dialcoxychroman 8 is reaffirmed.

Additionally, in the incubations in the presence of Fe-ascorbate it was confirmed that the hydroxy derivative fluorate 9 was an inhibitor of the lipidic peroxidation per se ($IC_{50}$=5.3 μM). However, the inhibiting activity of this compound was slightly inferior to that shown by hydroxychroman 6.

Figure 2:
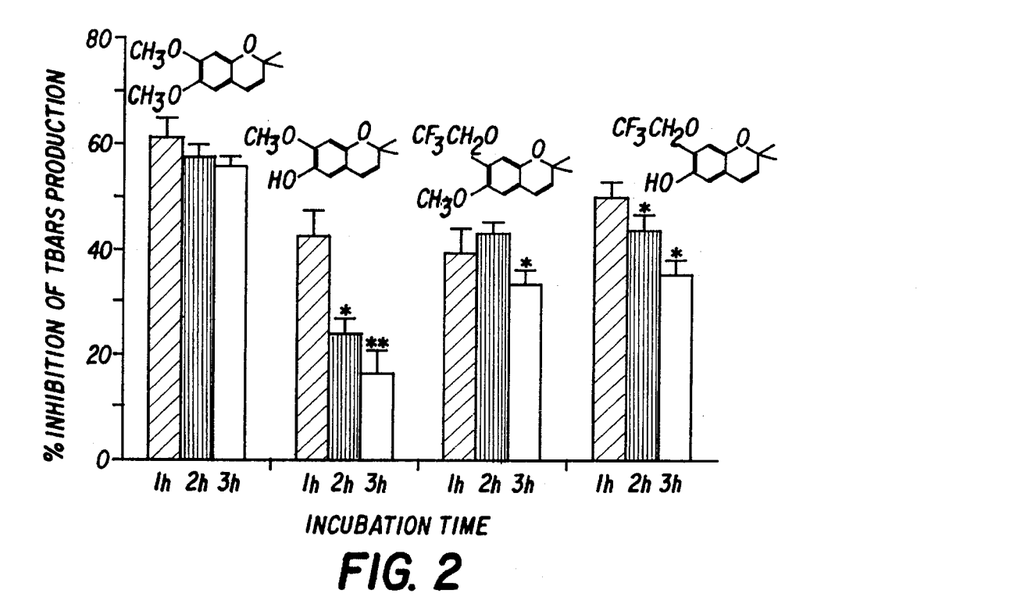
FIG. 2 is a graph of the effect of incubation time on the inhibition of lipid peroxidation in rat liver microsomes incubated with NADPH shown by the chromenes 5, 6, 8 and 9 at concentrations of 15, 1, 6 and 5 µM, respectively. The values shown are the average +/–SD of sextuplicate tieterminations that were performed. The difference between consecutive hours are marked by asterisks: * $P<0.001$, ** $P<0.005$.

From the foregoing results it may be deduced that the 2,2-dimethylchromans, fluorated or not, showed more elevated inhibiting activities of the lipidic peroxidation than their corresponding 2,2-dimethylchromenes. Therefore, four of these chromans (i.e. compounds 5, 6, 8 and 9) were chosen in order to study the persistence of the inhibiting activity. These inhibitors were incubated independently over three hours in the presence of NADPH employing concentrations near to their respective values of $IC_{50}$ and the results obtained are shown in FIG. 2. In the case of the non-fluorated compounds, while the inhibiting effect shown by the chroman 5 remains constant, the activity of the hydroxychroman 6 significantly decreases after the second and third hour of incubation. This drop may be the result of the deactivating metabolism suffered by said compound in the incubation medium. Furthermore, the fact that the activity of the dialcoxychroman 5 remained essentially unaltered throughout all of the experiment suggests the constant production of active species like antioxidants from said compound, that is to say, the metabolite 6. Consequently, the compound 5 may be utilized as an inhibitor of lipidic peroxidation with a potentially sustained mode of action.

With regard to the fluorate derivatives, the inhibiting effect produced by the chroman 8 was slightly higher during the second hour of incubation, which suggests the continued production of an active species, that is, the hydroxy derivative 9. Identification of this compound as a metabolite of compound 8 sustains this hypothesis. The significant drop in the inhibiting activity during the third hour may be due to a deceleration of the desalquilating metabolism which leads to the formation of species with antioxidant activity. It is interesting to note that the descent indicated is not significant when it is compared with the percentage of inhibition determined for the first hour of incubation (P>0.005). Therefore, this fluorated chroman shows itself as a potent inhibitor of the lipidic peroxidation with a sustained mode of action.

Additionally, as has been observed with hydroxychroman 6, the inhibiting activity of the compound 9 decreases during the second and the third hour of incubation. However, this drop was less pronounced than that obtained for the compound 6, which could indicate that the active species is more persistent in the incubation medium.

b) Evaluation of the lipidic peroxidation in liposomes.

Following, with minor modifications, the model proposed by Pelle et al.: Annals of the New York Academy of Sciences (1989) 570, 491–494,(herein incorporated by reference), 27 mg of lecithin of soy were weighed and 1.5 ml of phosphate buffer pH 7.4 (PBS) were added. The compounds studied as protectors from the lipidic peroxidation were added dissolved in ethanol in the quantity necessary to reach a 1% molar solution with respect to the lecithin present. In all cases multilamelar liposomes were obtained by mechanical agitation during one minute.

Once obtained, the liposomes both those incorporating anti-oxidants and those which do not incorporate them, were exposed to UV-C radiation (254 nm). A sample without containing anti-oxidants and not exposed to the radiation was prepared as a control. The UV-C radiation was utilized because it produces effects similar to those of UV-B but in a much shorter time. For example, one hour of UV-C irradiation would produce effects similar to seven hours of UV-B irradiation.

During the UV exposure portions were taken at different times in order to determine the amount of lipidic peroxidation.

TBARS Test. The lipidic peroxidation was done determining spectrophotometrically the increase in the production of substances which react with the thiobarbituric acid (TBARS). Briefly, 0.2 ml of liposomal suspension, 3 ml of trichloroacetic acid at 20% and 1 ml of thiobarbituric acid at 1% were incubated at 100° C. for 25 min. Afterward it was centrifuged at 2000 rpm for 10 minutes and the absorption was determined at 532 nm.

Figure 3:
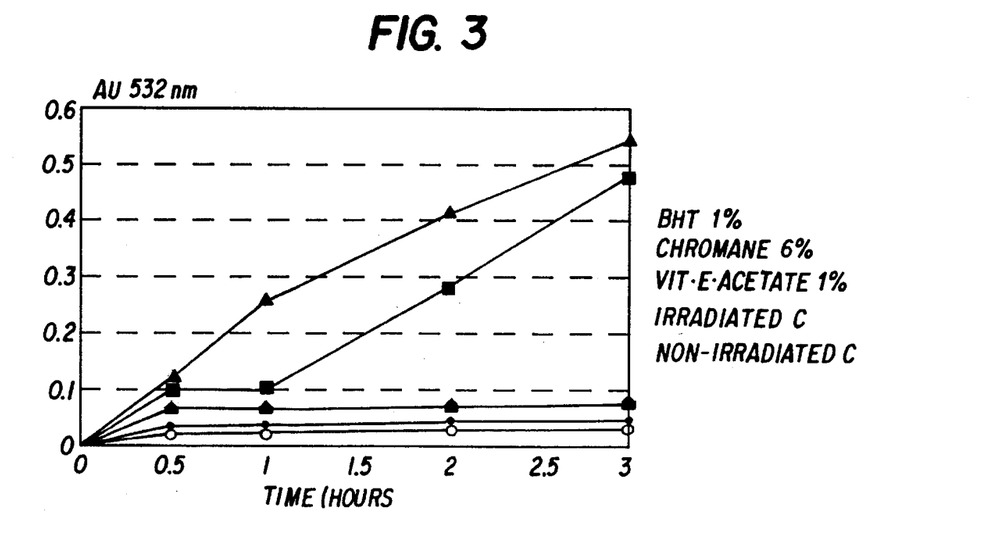
FIG. 3 is a graph of the increase of the lipidic peroxidation in liposomes of soy phosphatidyl choline as a function of the time of irradiation with UV-C and the presence of lipophilic anti-oxidants.

As is shown in FIG. 3, the irradiated liposomes exhibit a greater production of lipidic peroxides that the corresponding control not subjected to the UV-C radiation. Utilizing this model the power of protection against lipidic peroxidation induced by the chroman 6 was compared with respect to the vitamin E-acetate and to the BHT, recognized lipophilic anti-oxidants. The results indicate that the chroman 6 and the BHT have an potential inhibiting of lipidic peroxidation similar and notably superior to that shown by Vitamin E-acetate at the concentration tested.

EXAMPLE 2

Preparation of the liposomes encapsulating DXR

A chloroform solution was prepared containing the selected lipids (table II) and 7.5 mg. of the chroman 6 in a round-bottomed flask. Afterward proceeding to the elimination of the organic solvent by means of roto-evaporation, additionally the traces of solvent were eliminated by passage of $N_2$ or by lyophilization. The lipidic film thus obtained was hydrated, with 3 ml of NaCl solution at 0.9% containing DXR, by agitation in a vibromixer at intervals of 30 sec., followed by resting in a bath maintained at 60° C. for the same amount of time and an effective agitation up to 10 min. Thus a liposomal dispersion was obtained containing preferably multilamelar vesicles (MLVs). The liposomal solution was sonicated by ultrasonic irradiation by means of a titanium probe until a change in the turbidity was observed. The protocol of sonication was carried out in relays of 2 min. of sonication and one minute resting under atmosphere of $N_2$ in an ice water bath. In order to eliminate the particles of titanium produced during the sonication, it was centrifuged for 20 min. at 3000 rpm. The liposomal suspension thus obtained contained small unilamelar liposomes (SUVs).

Alternatively, the suspension of multilamelar liposomes obtained as described was submitted to extrusion through polycarbonate filters of 0.4 and 0.2 μm in diameter of pore subsequently, obtaining liposomes designated VET.

The determination of the percentage of encapsulation of DXR was done by chromatographic separation of a portion of the liposomal suspension, by means of Sephadex G-50M utilizing NaCl 0.9% as eluent.

In Table II the results of encapsulation for the different methods and compositions employed are shown. By means of the observation of these, it may be noted that the inclusion of a phospholipid with negative charge is necessary in order to obtain high percentages of encapsulation. Thus, in MLV or neutral SUV liposomes, with or without presence of cholesterol, the encapsulation of DXR arrived at a maximum at 15% of the initial quantity of the drug. In contrast, when phosphatidylglycerol was included in the lipidic composition the values of encapsulation were greater than 80% in all the tests conducted where the phosphatidylglycerol:DXR ratio was maintained equal to 5:1.5. When the proportion of DXR was increased in that ratio at 5:3 it resulted in a reduction of the encapsulated drug, confirming the necessity that in the preparation of liposomes a minimum quantity of phospholipid with a negative charge exists with respect to the DXR to be encapsulated.

Furthermore, it was observed that both phospholipids of natural origin, whether hydrogenated or not, and synthetics gave similar encapsulation results with the methods employed.

TABLE II

| TYPE | COMPOSITION | RATIO (mg) | % ENCAPSULATION |
|---|---|---|---|
| MLV | PC:DXR | 150:15 | 10 |
| MLV | PC:CHOL:DXR | 100:50:15 | 14 |
| MLV | PC:PG:CHOL:DXR | 50:50:50:15 | 80 |
| SUV | PC:CHOL:DXR | 100:50:15 | 15 |
| SUV | PL:PG:CHOL:DXR | 50:50:50:15 | 88 |
| SUV | PC:PG:CHOL:DXR | 50:50:50:15 | 90 |
| SUV | PC:PG:CHOL:DXR | 50:50:50:30 | 55 |
| SUV | DPPC:DPPG:CHOL:DXR | 50:50:50:15 | 85 |
| VET | PL:PG:CHOL:DXR | 50:50:50:15 | 87 |
| VET | PC:PG:CHOL:DXR | 50:50:50:15 | 89 |
| VET | DPPC:DPPG:CHOL:DXR | 50:50:50:15 | 87 |

The experiments were conducted in the presence of 7.5 mg. of the chroman 6.

EXAMPLE 3

Preparation of liposomes encapsulating DXR

Proceeding in a manner analogous to that described in EXAMPLE 2 to obtain VET liposomes utilizing a ratio by weight of PL:PG:CHOL:DXR of 50:50:50:15 and varying the anti-oxidant agent employed. The results obtained show (Table III) that no appreciable differences exist in the percentages of encapsulation when different inhibitors of the lipidic peroxidation were utilized.

TABLE III

| TYPE | COMPOUND | % ENCAPSULATION |
|---|---|---|
| VET | 1 | 89 |
| VET | 2 | 85 |
| VET | 3 | 87 |
| VET | 4 | 84 |
| VET | 5 | 86 |
| VET | 6 | 87 |
| VET | 7 | 88 |
| VET | 8 | 90 |
| VET | 9 | 83 |

Composition: PL:PG:CHOL:DXR (50:50:50:15)

EXAMPLE 4

In vivo studies (I).

As in Example 1, VET liposomes of composition PL:PG:CHOL:DXR (50:50:50:15) and chroman 6 (7.5 mg) were prepared.

Figure 4:
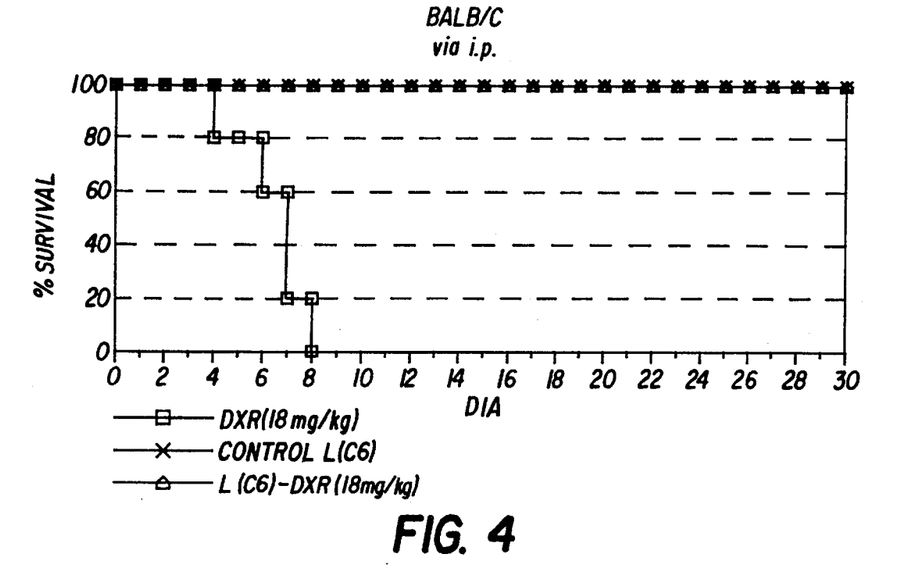
FIG. 4 represents curves of survival in healthy BALB/C rats for the i.p. administration of L(C6), L(C6)-DXR and F-DXR.

Inoculation by intraperitoneal route. Healthy BALB/C rats were treated intraperitoneally with said preparation, and the survival curves compared (FIG. 4) with the administration of free drug at the same dose, 18 mg/kg. In the experiment there was incorporated as a control a preparation of liposomes without drug, of identical characteristics and at the same lipidic concentration which would correspond to the liposomes with DXR.

Figure 5:
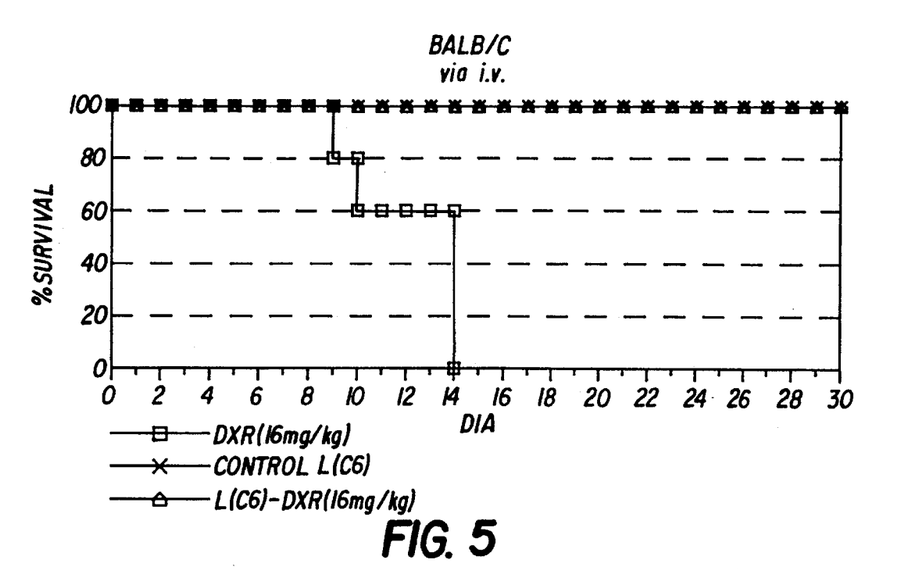
FIG. 5 represents survival curves in healthy BALBC rats for the i.v. administration of L(C6), L(C6)-DXR and F-DXR.

Inoculation intravenously. Healthy BALB/C rats were treated intravenously with the preparation of L-DXR described and the survival curves compared (FIG. 5) with the administration of free drug of the same dose, 16 mg/kg. In the experiment there was incorporated as a control a preparation of liposomes without drug, of identical characteristics and at the same lipidic concentration which would correspond to the liposomes with DXR.

The results obtained from the survival curves, both in the i.p. inoculation and in the i.v., indicated absence of toxicity of the liposomes per se, that is, of those which did not contain the drug. Likewise, no mortality was produced when the DXR was administered in liposomes. In contrast, when the same doses of DXR were inoculated i.p. or i.v. in the form of free drug, a 100% mortality was observed during the second week subsequent to the administration.

EXAMPLE 5

In vivo studies (II)

As in Example 1, VET liposomes of composition PL:PG:CHOL:DXR (50:50:50:15) and chroman 6 (7.5 mg) were prepared.

Analogously, VET liposomes of composition PL:PG:CHOL:DXR (50:50:50:15) were prepared without incorporating the anti-oxidant.

Inoculation by intraperitoneal route. Healthy B6D2F1 rats were treated intraperitoneally with the preparation of L-DXR containing the chroman 6 and the survival curves compared (FIG. 6) with the administration of encapsulated drug, in the absence of the anti-oxidant, at the same dose of 24 mg/kg. In the experiment there was incorporated as a control a preparation of liposomes, without drug but with the chroman 6, of identical characteristics and at the same lipidic concentration which would correspond to the liposomes with DXR.

The results obtained from the survival curves indicated absence of toxicity of the liposomes per se, that is, of those which did not contain the drug. Likewise, a clear reduction of the toxicity of the DXR was observed in the liposomal preparation which contained the chroman 6, passing from a 20% survival in the absence thereof to a survival of 60% in its presence.

Although only preferred embodiments are specifically illustrated and described herein, it will be appreciated that many modifications and variations of the present invention are possible in light of the above teachings and within the purview of the appended claims without departing from the spirit and intended scope of the invention.

We claim:

1. Liposomes encapsulating doxorubicin, comprising lipids, doxorubicin and a compound of general formula A or B:

-continued wherein $R_1$ and $R_2$ are the same or different and are independently selected from the group consisting of HO—, CH3—, $CF_3CH_2O$—, and $CH_3O$—.

2. Liposomes encapsulating doxorubicin according to claim 1, wherein the compound is selected from formula 1 or 5:

3. Liposomes encapsulating doxorubicin according to claim 1, wherein the compound is selected from formula 2 or 6:

4. Liposomes encapsulating doxorubicin according to claim 1, wherein the compound is selected from formula 7:

5. Liposomes encapsulating doxorubicin according to claim 1, wherein the compound is selected from formula 3 or 8:

6. Liposomes encapsulating doxorubicin according to claim 1, wherein the compound is selected from formula 4 or 9:

7. Liposomes encapsulating doxorubicin according to claim 1 wherein the ratio of total lipids forming the liposomes to doxorubicin is between 20:1 and 2:1.

8. Liposomes encapsulating doxorubicin according to claim 1 wherein the lipids comprising the liposomes are cholesterol and phospholipids, said phospholipids are selected from the group consisting of naturally occurring phospholipids, synthetically derived phospholipids and mixtures thereof.

9. Liposomes encapsulating doxorubicin according to claim 8, wherein the phospholipids are a mixture of negatively charged and neutral phospholipids.

10. Liposomes encapsulating doxorubicin according to claim 9 wherein the ratio of neutral phospholipid and the negative charged phospholipids falls between 10:2 and 10:10 respectively.

11. Liposomes encapsulating doxorubicin according to claim 8 wherein the proportion of cholesterol, with respect to the quantity of total lipids, is between 0 and 50%.

12. Liposomes encapsulating doxorubicin according to claim 1 wherein the ratio of the compound to total lipids is between 0.01 and 15%.

13. Liposomes encapsulating doxorubicin according to claim 7 wherein the ratio of total lipids forming the liposomes to doxorubicin is preferably 10:1.

14. Liposomes encapsulating doxorubicin according to claim 10 wherein the ratio of neutral phospholipid and the negative charged phospholipids is preferably between 10:7 and 10:10 respectively.

15. Liposomes encapsulating doxorubicin according to claim 11 wherein the proportion of cholesterol, with respect to the quantity of total lipids, is between 35% and 50%.

16. Liposomes encapsulating doxombicin according to claim 12 wherein the ratio of the compound to total lipids is between 0.1 and 10%.

17. A doxorubicin containing composition comprising Doxorubicin, lipid and a compound, the protecting compound being selected from the 2,2-dimethyl chromans and 2,2-dimethylchromenes.

18. The composition of claim 17 wherein the lipid is selected from the group consisting of phospholipids and sterols.

19. The composition of claim 17 wherein the compound is of general formula A or B:

and wherein $R_1$ and $R_2$ are the same or different and are independently selected from the group consisting of HO—, $CH_3$—, $CF_3CH_2O$—, and $CH_3O$—.

20. The composition of claim 17 wherein the ratio of lipids to doxorubicin is between 20:1 and 2:1.

21. The composition of claim 17 wherein the ratio of lipids to compound is between 0.01 and 15%.

22. A method of treating cancer comprising administering a pharmaceutically effective amount of a pharmaceutical composition comprising doxorubicin, lipid and a compound of general formula A or B:

A

B wherein $R_1$ and $R_2$ are the same or different and are independently selected from the group consisting of HO—, $CH_3$—, $CF_3CH_2O$—, and $CH_3O$—.

23. A method of reducing chemically induced free-radical or oxidative reactions of lipids comprising administering a pharmaceutically effective amount of a compound of general formula A are B:

wherein $R_1$ and $R_2$ are the same to different and are independently selected from the group consisting of HO—, $CH_3^{13}$, $CF_3CH_2O$—, $CH_3O$—, encapsulate in a liposome to an organism.

* * * * *

UNITED STATES PATENT AND TRADEMARK OFFICE
CERTIFICATE OF CORRECTION

PATENT NO. : 5,605,703
DATED : February 25, 1997
INVENTOR(S) : Fernando P. Lambiez et al.

It is certified that error appears in the above-identified patent and that said Letters Patent is hereby corrected as shown below:

In the drawings:
Delete Figs. 2 and 3, and substitute therefor Figs. 2 and 3, as follows:

FIG. 2

UNITED STATES PATENT AND TRADEMARK OFFICE
CERTIFICATE OF CORRECTION

PATENT NO.   : 5,605,703                             Page 2 of 2
DATED        : February 25, 1997
INVENTOR(S)  : Fernando P. Lambiez et al.

It is certified that error appears in the above-identified patent and that said Letters Patent is hereby corrected as shown below:

Signed and Sealed this

First Day of September, 1998

*Attest:*

BRUCE LEHMAN

*Attesting Officer*    Commissioner of Patents and Trademarks